United States Patent [19]
DeBring

[11] Patent Number: 5,176,667
[45] Date of Patent: Jan. 5, 1993

[54] LIQUID COLLECTION APPARATUS

[76] Inventor: Donald L. DeBring, 679 Crestview Ave., Camarillo, Calif. 93010

[21] Appl. No.: 873,996

[22] Filed: Apr. 27, 1992

[51] Int. Cl.⁵ .............................................. A61B 19/00
[52] U.S. Cl. ..................... 604/356; 4/144.1; 604/317
[58] Field of Search ........... 604/317, 356, 357; 4/144.1, 144.2, 144.3, 455, 451

[56] References Cited

U.S. PATENT DOCUMENTS

| | | | |
|---|---|---|---|
| 930,439 | 8/1909 | Topping | 604/356 |
| 3,757,356 | 9/1973 | Freeman | 604/356 |
| 3,763,857 | 10/1973 | Schrading | 604/356 |
| 3,928,875 | 12/1975 | Persson | 4/144.2 |
| 4,455,140 | 6/1984 | Joslin | 604/317 |
| 4,679,590 | 7/1987 | Hergenroeder | 604/356 |
| 4,725,270 | 2/1988 | Schuldt et al. | 604/356 |
| 4,747,166 | 5/1988 | Kuntz | 4/455 |
| 4,752,293 | 6/1988 | Smith | 604/356 |
| 4,870,710 | 10/1989 | Hartmann | 4/455 |
| 5,034,006 | 7/1991 | Hosoda et al. | 604/356 |

*Primary Examiner*—Paul J. Hirsch
*Attorney, Agent, or Firm*—Jack C. Munro

[57] ABSTRACT

A liquid collection apparatus for collecting expelled liquid from a localized source. The parts of the apparatus that are wetted by the expelled liquid are disposable. A non-absorbing pad is utilized which has liquid directing channels which direct the expelled liquid into a manifold and from the manifold into a conduit. The conduit is connected with a peristaltic pump with the expelled liquid being moved through the conduit into a collection reservoir.

7 Claims, 2 Drawing Sheets

LIQUID COLLECTION APPARATUS

BACKGROUND OF THE INVENTION

1. Field of the Invention

The field of this invention relates to liquid collection apparatuses and more particularly to a liquid collection apparatus which is to collect liquid that is being expelled from a localized source, the source being potentially hazardous, the liquid being collected within a collecting chamber and upon achieving complete collection, the liquid as well as all parts that are being wetted by the liquid are to be disposed of.

2. Description of Prior Art

The subject matter of this invention is going to be discussed as a medical device and more particularly to a medical device that is to be used in conjunction with surgical procedures where irrigation and body liquid are expected to be discharged during the procedure. However, it is considered to be within the scope of this invention that this invention could be utilized in any environment where collection of localized cumulative liquid is required.

In a hospital operating room, emergency room, or even in a doctor's office, when surgery is performed, there will be discharged liquids. Irrigation liquids such as saline solutions are constantly being used. The main discharge in conjunction with surgery from the patient would be blood. The blood could potentially be a carrier of disease.

At the present time, when surgery is being performed, it is common to place the surgical area of the patient on a sterile cloth, one or two towels being located under the cloth. During the surgical procedure, the cloth and towels get saturated and the liquids drip from there onto a table, floor as well in contact with the doctors and nurses located in this surgical facility. When the surgical procedure is completed, maintenance people remove the cloth and towels, clean and wipe off the table, and clean and mop the floor. This type of practice exposes the maintenance staff as well as the doctors and nurses to the potentially infectious liquids that have been discharged.

When surgery is being performed on a hand, arm, foot, leg or head, the amount of liquids that are discharged is relatively minimal compared to the amount that would be discharged when surgery is performed on the chest and abdomen. The hazard from the liquids from chest and abdominal surgery is greatly compounded because of the quantity of the liquids that are discharged. The patient is covered with drapes that are designed to expose just the surgical area. The discharged liquids flow underneath the drapes to possibly a non-sterile area and then wick back up the drape to again come in contact with the sterile field and contaminate such. The liquids flow along the relatively non-absorbent surface of the drapes onto the floor, onto the gowns of the medical personnel, saturating both the gowns and often the undergarments of the medical personnel exposing that personnel to direct contact with these liquids. Besides the significant health hazards that these liquids impose on the personnel, the liquids on the floor will inherently make a slippery mess which may cause the personnel to slip and fall.

SUMMARY OF THE INVENTION

The structure of the present invention comprises a flat sheet material pad which is formed of a non-absorbent material. The pad can be formed in various configurations and of various sizes with it being understood that a pad for use in surgery of the hand would be quite smaller than the pad utilized in surgery of the chest. The pad is soft, resilient and non-absorbent to liquid. The pad includes liquid directing channels which direct the liquid into a manifold. The manifold is connected to a vacuum source through a liquid outlet conduit. The pad is readily disengageable from the liquid outlet conduit so that the conduit may be connected to various sizes of pads or a particular pad may be removed and a new pad installed if such is deemed to be desired. The conduit constitutes a flexible walled tube with this tube being connected to a peristaltic pump. From the pump, the flexible walled tubular conduit connects to a collection chamber which is generally in the form of a flexible walled bag. This bag is vented to the atmosphere. All parts which are wetted by the liquid are to be disposed of which comprises all parts of the apparatus with the exception of the pump.

The primary objective of the present invention is to confine and collect potentially hazardous liquid that is being emitted from a localized source so as to diminish the possibility of exposure to personnel of disease bearing body liquids.

Another objective of the present invention is to permit disposing of the wetted parts of the apparatus of the present invention without requiring disassembly of these parts, thereby minimizing potential contact by the personnel with hazardous liquids.

Another objective of the present invention is to construct a liquid collection apparatus which functions to keep the sterile operating field, during a surgical procedure, as clean as possible.

Another objective of the present invention is to construct a liquid collection apparatus which diminishes the chance of body liquids contaminating the clothing and body of the medical personnel.

Still another objective of the liquid collection apparatus of the present invention is to reduce exposure of other personnel such as maintenance, janitorial and laundry to the hazard of the potentially disease-ridden liquids.

DETAILED DESCRIPTION OF THE SHOWN EMBODIMENT

Referring particularly to the drawings there is shown the collection apparatus 10 of this invention. The collection apparatus 10 comprises a pad assembly 12, a pump 14, and a collection reservoir 16.

Figure 1:
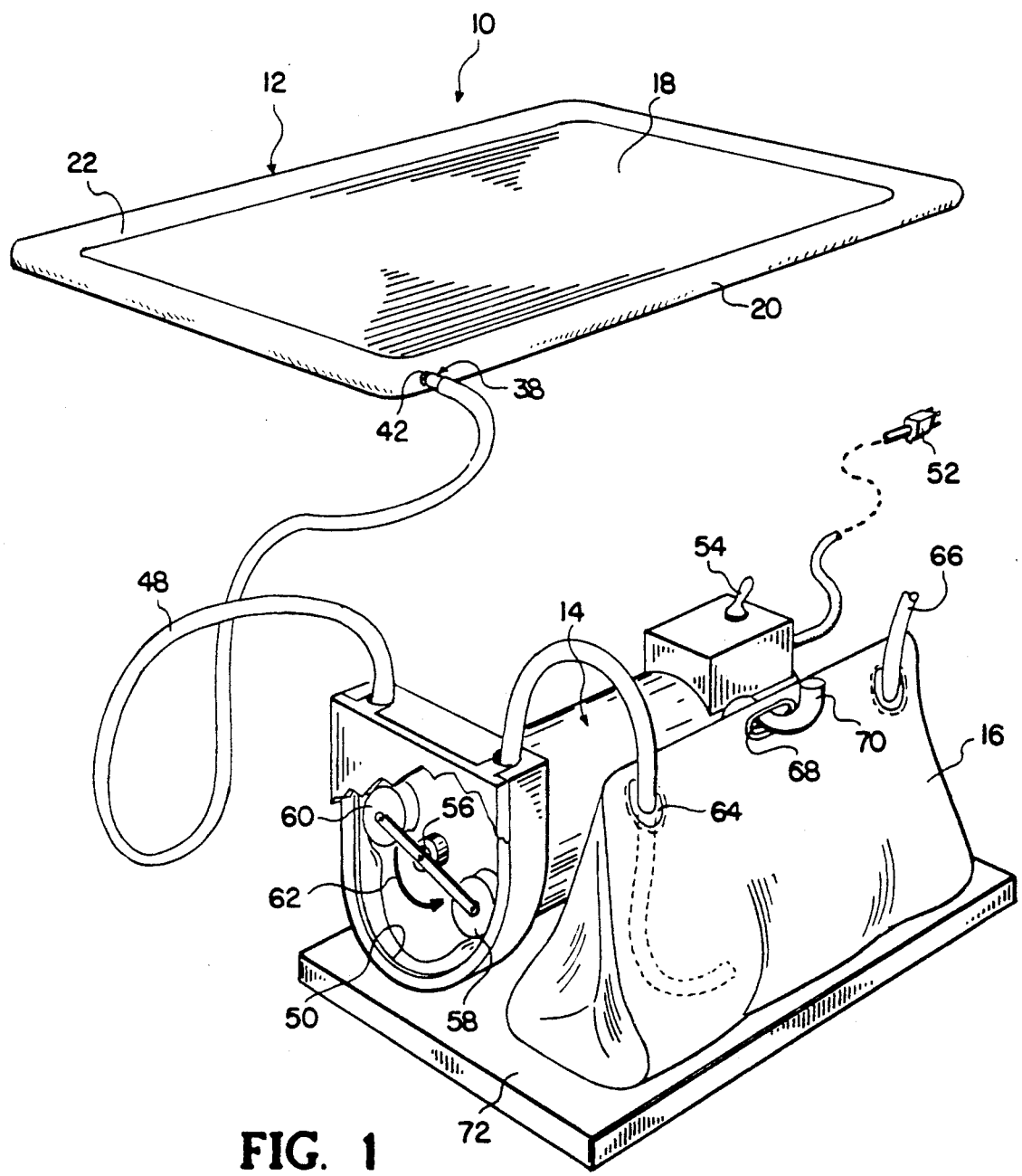
FIG. 1 is an isometric view of the liquid collection apparatus of the present invention.
Figure 2:
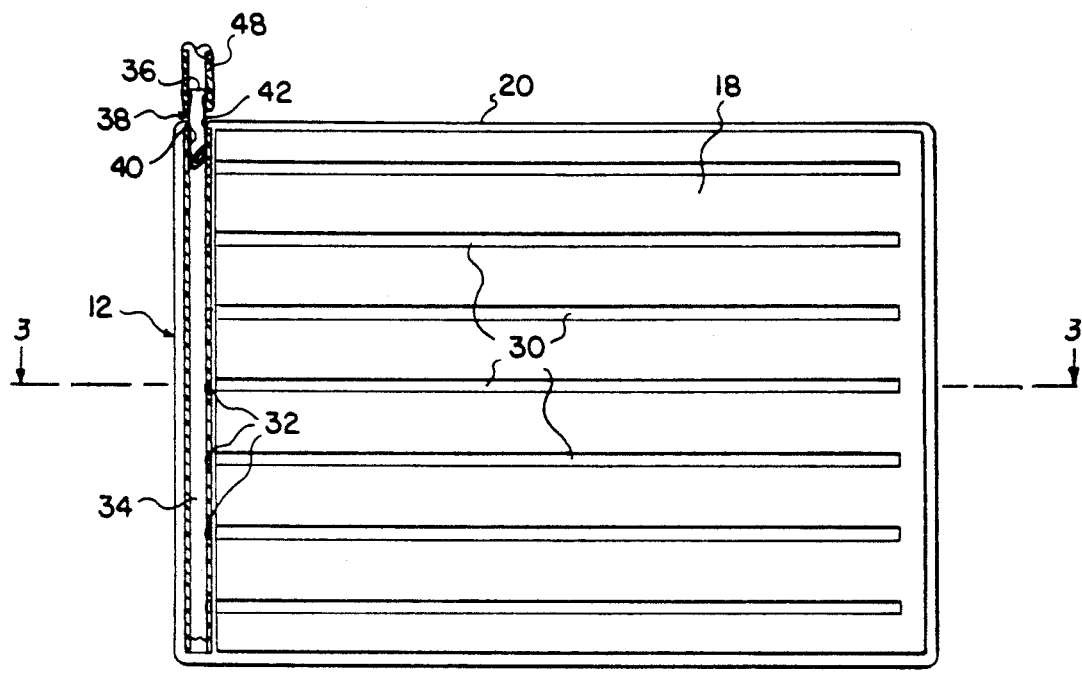
FIG. 2 is a bottom internal view of the pad used in conjunction with the liquid collection apparatus of this invention.
Figure 3:
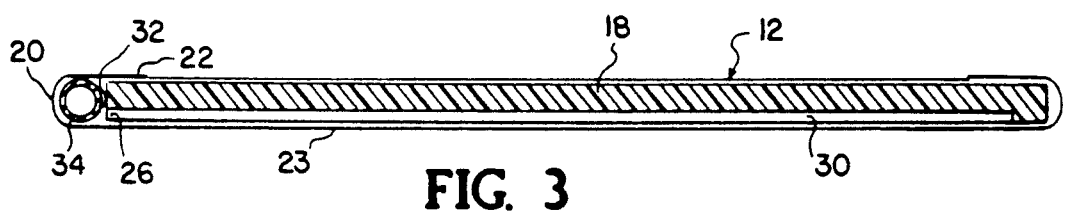
FIG. 3 is a cross-sectional view taken along line 3—3 of FIG. 2 showing in more detail the construction of the pad.
Figure 4:
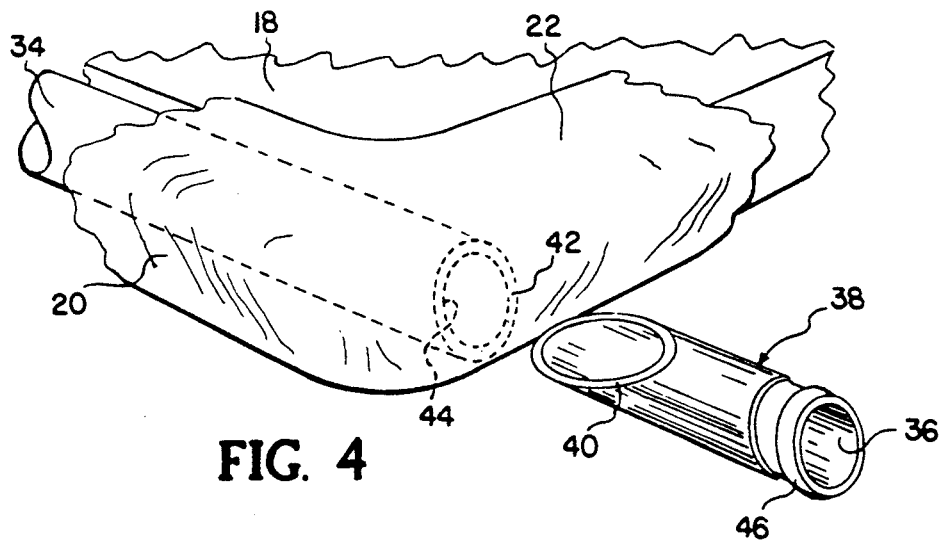
FIG. 4 is an exploded view depicting more clearly the connection between the liquid conducting tube and the pad of the apparatus of the present invention.

The pad assembly 12 comprises a non-absorbent resilient pad 18 which has a planar upper surface and which is enclosed within a flexible sheet material, perimeter frame 20. Frame 20 could be thin plastic sheet. Pad 18 is to be constructed of a liquid permeable material that is readily able to conduct liquid therethrough but not retain it. A typical material of construction of the pad 18 would be some form of a plastic. The size of the pad 18 is variable and in actual practice various sizes will be utilized. It is the intention, in referring to FIG. 1, that on the planar upper surface of the pad 18 a body part such as a hand, an arm, a leg, a foot is to placed on this planar upper surface of the pad 18. If the pad 18 is large enough, the torso section of a human could be located on the planar upper surface of the pad 18.

The upper surface of the perimeter sidewall 20 is folded over at a right angle forming an inwardly extending flange 22. This flange 22 is secured by adhesive or heat sealing to pad 18 and is what holds the pad 18 in position within the confines of the sidewall 20. Along the bottom surface of the pad 18 there is formed a closed bottom wall 23 which is integral to the sidewall 20. The liquid is designed to readily flow through the pad 18 into channels 30 formed in the bottom surface of the pad 18. This liquid is intended to flow along the channels 30 and along the bottom surface of the bottom wall 23 and into holes 32 formed within manifold tube 34 mounted at the inner end 26 of the bottom wall 23 and the pad 18. There will normally be a hole 32 for each channel 30. Also, instead of holes 32, there may be used an elongated slot.

The liquid that comes to rest within the tube 34 is to be conducted into passage 36 formed within connector 38. Connector 38 has a sharp pointed tubular end 40 that is to penetrate side wall 20 and be inserted through hole 42 now formed within the sidewall 20 and into hole 44 formed in tube 34 with a liquid-tight connection being established between tube 34, end 40 and sidewall 20. The liquid that comes to rest within the tube 34 will flow into passage 36. The connector 38 also includes an enlarged annular end 46 which is to engag in a liquid-tight manner with a flexible tubular rubber or plastic conduit 48. The conduit 48 fits within a pumping chamber 50 of the peristaltic pump 14. The pump 14 is to be electrically driven by an electrical conduit 52 and activated by on/off switch 54. The pump 14 can comprise any conventional type of pumps such as model number 7021-24 which is electrically driven by a motor model number 7543-60, manufactured by Barnant Company of Barrington. Ill.

Operation of the pump causes rotation of shaft 56 which in turn rotates rollers 58 and 60. The rollers 58 and 60 applies a squeezing action on the conduit 48. The rollers 58 and 60 are rotatably driven in the direction of arrow 62. The progressive squeezing action applied by rollers 58 and 60 to the conduit 48 will tend to move any liquid within the conduit 48 into collection reservoir 16. Conduit 48 is connected by a slip joint 64 in a liquid-tight manner and extends with reservoir 16. Collection reservoir 16 comprises a flexible walled bag resembling a conventional woman's purse. Associated also with the collection reservoir 16 is a vent tube 66 which vents the interior of the collection reservoir 16. The collection reservoir 16 has a mounting opening 68 which connects to a rod 70. The opening 68 is to fixedly position the collection reservoir 16 on the rod 70 and also fixedly position the collection reservoir 16 on an optionally used base 72. The pump 14 is also mounted on the base 72.

It is to be understood that after a single usage the pad assembly 12, the conduit 48, as well as the collection reservoir 16 is to be discarded. The only structure that would not be discarded after a single usage would be the pump 14 and the base 72 (if used). It is to be understood that the conduit 48 is readily disengagable from the pumping chamber 50. A new unused conduit 48 can also be readily engaged within the pumping chamber 50.

It is considered to be within the scope of this invention that the pad assembly 12 could be constructed of a different shape than what is shown. For example, a U-shaped configuration may be desireable in certain instances

What is claimed is:

1. A liquid collection apparatus comprising:
    a pad having liquid directing means, said pad being adapted to receive expelled liquid from a source;
    a manifold conduit contained within said pad, said manifold conduit to receive said expelled liquid from said liquid-directing means;
    outlet conduit having a connector with a sharp pointed tubular end, said sharp pointed tubular end to penetrate said sidewall of said pad establishing a liquid-tight connection therebetween while also establishing a liquid-tight connection with said manifold conduit;
    pump means connected to said liquid outlet conduit, said pump means for creating a vacuum in said liquid outlet conduit and moving said expelled liquid through said liquid outlet conduit; and
    a collection reservoir connected to said pump means and said liquid outlet conduit, said expelled liquid flowing through said liquid outlet conduit is to be deposited in said collection reservoir, whereby said pad and said liquid outlet conduit plus said collection reservoir being disposable after a single usage.

2. The liquid collection apparatus as defined in claim wherein said liquid directing means comprising a plurality of channels, said channels being adapted to receive said expelled liquid and direct such to a collection manifold, said collection manifold being connected directly to said outlet conduit.

3. The liquid collection apparatus as defined in claim 1 wherein said pad being non-absorbing of liquid.

4. The liquid collection apparatus as defined in claim 1 wherein said connector being readily disengagable from said manifold conduit so as to permit various sizes of said pads to be installable with said outlet conduit.

5. The liquid collection apparatus as defined in claim 1 wherein said pump means comprising a peristaltic pump.

6. The liquid collection apparatus as defined in claim 1 wherein said collection reservoir being vented to the ambient.

7. The liquid collection apparatus as defined in claim 6 wherein said collection reservoir comprising a flexible walled bag.

* * * * *